(12) United States Patent
Uematsu et al.

(10) Patent No.: US 7,019,163 B2
(45) Date of Patent: Mar. 28, 2006

(54) PROCESS FOR PRODUCING PERFLUOROVINYLCARBOXYLIC ACID ESTER

(75) Inventors: Nobuyuki Uematsu, Fuji (JP); Masanori Ikeda, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/481,256

(22) PCT Filed: Jun. 28, 2002

(86) PCT No.: PCT/JP02/06584

§ 371 (c)(1),
(2), (4) Date: Jul. 13, 2004

(87) PCT Pub. No.: WO03/002505

PCT Pub. Date: Jan. 9, 2003

(65) Prior Publication Data

US 2005/0014969 A1    Jan. 20, 2005

(30) Foreign Application Priority Data

Jun. 29, 2001    (JP)    ............................. 2001-198039

(51) Int. Cl.
*C07C 69/52*    (2006.01)

(52) U.S. Cl. ...................................... 560/227; 560/226

(58) Field of Classification Search ................ 560/226, 560/227, 179, 181, 183, 184, 205, 219; 562/579, 562/586, 598, 602, 605
See application file for complete search history.

(56) References Cited

U.S. PATENT DOCUMENTS

| | | | |
|---|---|---|---|
| 3,546,186 A | 12/1970 | Gladding et al. | |
| 3,641,104 A | 2/1972 | Anderson et al. | |
| 4,138,426 A | 2/1979 | England | |
| 4,153,804 A * | 5/1979 | Yamabe et al. | ............. 560/183 |
| 4,275,226 A | 6/1981 | Yamabe et al. | |
| 4,340,750 A | 7/1982 | Yamabe et al. | |
| 4,675,453 A | 6/1987 | Resnick | |

FOREIGN PATENT DOCUMENTS

| | | |
|---|---|---|
| JP | 42-24565 | 11/1967 |
| JP | 45-22327 B1 | 7/1970 |

* cited by examiner

*Primary Examiner*—Johann Richter
*Assistant Examiner*—Karl Puttlitz
(74) *Attorney, Agent, or Firm*—Birch, Stewart, Kolasch & Birch, LLP

(57) ABSTRACT

The present invention relates to a method for producing a perfluorovinylcarboxylic acid ester by reacting a perfluorovinylcarboxylic acid salt with an alkylating agent. The present invention provides a method to produce perfluorovinylcarboxylic acid ester, which is used as a raw material of an ion-exchange membrane for the chloro alkali process, in high yield from starting material, a compound which can be easily produced, in a simple manner.

8 Claims, No Drawings

PROCESS FOR PRODUCING PERFLUOROVINYLCARBOXYLIC ACID ESTER

TECHNICAL FIELD

The present invention relates to a method for producing perfluorovinylcarboxylic acid ester, which is a raw material for perfluorocarboxylic acid polymer useful as a diaphragm material for the chloro alkali process. More specifically, the present invention relates to a method for obtaining perfluorovinylcarboxylic acid ester in improved yield by reacting perfluorovinylcarboxylic acid salt with an alkylating agent.

BACKGROUND ART

In the chloro alkali process, which produces caustic soda and chlorine, an ion-exchange membrane process is widely adopted, and a laminated type of membrane comprising a perfluorosulfonic acid polymer and a perfluorocarboxylic acid polymer is usually used as an ion-exchange membrane, which is a diaphragm for the process. In general, the perfluorocarboxylic acid polymer having a structure represented by the following general formula (5):

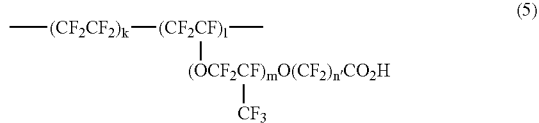

(wherein k/l=3–15, m=0–1, n'=1–5, each of k, l, m and n' is an integer, respectively), are used therein.

Among them, those with n'=2–3 are usually used. This polymer can be obtained by the hydrolysis reaction of the film of the copolymer of perfluorovinylcarboxylic acid ester represented by the following general formula (6):

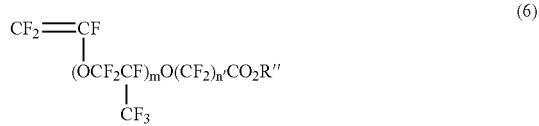

(wherein m=0–1, n'=1–5, each of m and n' respectively represent an integer, and R" represents an alkyl group having 1–4 carbon atoms) and tetrafluoroethylene (TFE).

Heretofore, various methods have been proposed as a method for producing perfluorovinylcarboxylic acid ester. For example, Japanese laid-open publication No. 52-78827 discloses a method for producing perfluorovinylcarboxylic acid ester represented by the following general formula (2):

$$CF_2=CFO(CF_2)_nCO_2R \quad (2)$$

(wherein n represents an integer of 2–3, and R represents an alkyl group having 1–4 carbon atoms (i.e. m=0 and n'=2–3 in the above described general formula (6))), wherein a compound represented by the general formula (4) mentioned below, a starting material, is saponified in the acid fluoride moiety thereof to obtain its alkaline metal salt, and the alkaline metal salt is further subjected to a thermal decomposition reaction to obtain perfluorovinylcarboxylic acid ester. In this process, however, it is difficult to obtain perfluorovinylcarboxylic acid ester in a satisfying yield because various kinds of byproducts are produced.

For avoiding such side reactions, for example, a method wherein a vinyl group is formed through a dehalogenation reaction of a precursor having a $ICF_2CF_2O$— structure (Japanese laid-open publication No. 55-31004), and a method wherein a vinylether compound having a terminal $CH_3OCF_2CF_2$— group is treated with a strong acid to introduce an ester group (Japanese laid-open publication No. 60-156632) have been proposed. These methods, however, have various problems in that it is needed, for example, to use expensive raw materials requiring multiple steps.

Japanese publication of examined application No. 45-22327 and Journal of Organic Chemistry 34, 1841(1969) disclose a method for obtaining perfluorovinylcarboxylic acid ester (a compound with n=2–12 in the general formula (2)), wherein a perfluorodicarboxylic acid salt (a compound with n=2–12 in the general formula (3) mentioned below) is thermally decomposed at 175–200° C. in the absence of solvent under anhydrous conditions to obtain perfluorovinylcarboxylic acid salt (a compound with n=2–12 in the following formula (1)), and subsequently the perfluorovinylcarboxylic acid salt is converted into a perfluorovinylcarboxylic acid by treating with an acid followed by reacting with an alcohol to obtain a perfluorovinylcarboxylic acid ester. In the method described in the publication of examined application, the manner to obtain the perfluorovinylcarboxylic acid ester from the perfluorovinylcarboxylic acid salt needs 2 steps of 1) producing the perfluorovinycarboxylic acid from the perfluorovinylcarboxylic acid salt by the acid treatment, and 2) producing the perfluorovinylcarboxylic acid ester by reacting the perfluorovinylcarboxylic acid with the alcohol. In addition, yield of perfluorovinylcarboxylic acid ester is very low. Further, the method has another drawback in that it requires a complicated purifying and separating process such as washing with a large volume of water to separate the perfluorovinylcarboxylic acid ester from the alcohol.

The inventors, after an extended study to solve the above described problems, found out a method to obtain a high-purity perfluorovinylcarboxylic acid ester in good yield, through less steps, by reacting perfluorovinylcarboxylic acid salt represented by the general formula (1) with an alkylating agent, and accomplished the present invention.

DISCLOSURE OF THE INVENTION

To achieve the object mentioned above, the present inventors carried out extensive investigations. As a result, it was found that a perfluorovinylcarboxylic acid ester can be obtained in good yield by a simple manner; reacting perfluorovinylcarboxylic acid salt with an alkylating agent. Thus, the present invention provides:

1. A method for producing a perfluorovinylcarboxylic acid ester, wherein a perfluorovinylcarboxylic acid salt represented by a following general formula (1):

$$CF_2=CFO(CF_2)_nCO_2M \quad (1)$$

(wherein n represents an integer of 2–3; and M represents an alkaline metal, an alkaline-earth metal, a quaternary ammonium group or a quaternary phosphonium group), is reacted with an alkylating agent to obtain a perfluorovinylcarboxylic acid ester represented by a following general formula (2):

$$CF_2=CFO(CF_2)_nCO_2R \tag{2}$$

(wherein n represents an integer of 2–3; and R represents an alkyl group having 1–4 carbon atoms).

2. The method for producing a perfluorovinylcarboxylic acid ester according to 1, wherein the perfluorovinylcarboxylic acid salt represented by the general formula (1) is produced by a thermal decomposition of perfluorodicarboxylic acid salt represented by a following general formula (3):

$$MOCOCF(CF_3)O(CF_2)_nCO_2M \tag{3}$$

(wherein n represents an integer of 2–3; and M represents an alkaline metal, an alkaline-earth metal, a quaternary ammonium group or a quaternary phosphonium group).

3. The method for producing a perfluorovinylcarboxylic acid ester according to 2, wherein the thermal decomposition of perfluorodicarboxylic acid salt represented by the general formula (3) is carried out in the presence of an aprotic polar solvent.

4. The method for producing a perfluorovinylcarboxylic acid ester according to 2 or 3, wherein the perfluorodicarboxylic acid salt represented by the general formula (3) is produced from an acid fluoride represented by the following general formula (4):

$$FCOCF(CF_3)O(CF_2)_nCO_2R' \tag{4}$$

(wherein n represents an integer of 2–3; and R' represents an alkyl group having 1–4 carbon atoms), and an alkaline substance.

5. The method for producing a perfluorovinylcarboxylic acid ester according to 2 or 3, wherein the perfluorodicarboxylic acid salt represented by the general formula (3) is produced by reacting an acid fluoride represented by the following general formula (4):

$$FCOCF(CF_3)O(CF_2)_nCO_2R' \tag{4}$$

(wherein n represents an integer of 2–3; and R' represents an alkyl group having 1–4 carbon atoms), with an alkaline substance.

6. The method for producing a perfluorovinylcarboxylic acid ester according to 2 or 3, wherein the perfluorodicarboxylic acid salt represented by the general formula (3) is produced by reacting an acid fluoride represented by the following general formula (4):

$$FCOCF(CF_3)O(CF_2)_nCO_2R' \tag{4}$$

(wherein n represents an integer of 2–3; and R' represents an alkyl group having 1–4 carbon atoms), with an alcohol to obtain carboxylic acid diester and saponifying the thus-obtained carboxylic acid diester with an alkaline substance containing M shown in the general formula (3).

BEST MODE FOR CARRYING OUT THE INVENTION

Firstly, a method for producing the perfluorovinylcarboxylic acid ester represented by the general formula (2) from the perfluorovinylcarboxylic acid salt represented by the general formula (1) and the alkylating agent will be described below.

As the alkylating agent used in the present invention, no particular limitation is imposed on them and various kinds of alkylating agents, which can alkylate a fluorinated carboxylic acid salt, are usable. Examples of such alkylating agents include alkyl esters of various strong acids and alkyl halides. Since perfluorocarboxylic acid ester represented by the general formula (2) produced according to the method of the present invention has an alkyl group having 1–4 carbon atoms, the alkyl group of the alkylating agent used herein has an alkyl group having 1–4 carbon atoms. Examples of such alkyl groups include methyl group, ethyl group, n-propyl group, i-propyl group, n-butyl group, s-butyl group and t-butyl group. Among them, methyl group and ethyl group are preferable from the viewpoint of, for example, efficiency in distillation, and methyl group is more preferable. Further, an alkyl group wherein hydrogen atoms are partially substituted with fluorine atom(s) may also be used. For example, partially fluorinated alkyl groups such as $CF_3CH_2-$, $CF_3CF_2CH_2-$ and $(CF_3)_2CH-$ may be used as the alkyl group.

Specific examples of the alkylating agents to be used in the present invention include p-toluenesulfonic esters such as methyl p-toluenesulfonate, ethyl p-toluenesulfonate and butyl p-toluenesulfonate; fluoroalkyl sulfonic esters such as methyl trifluoromethanesulfonate and ethyl trifluoromethanesulfonate; sulfuric esters such as dimethyl sulfate and diethyl sulfate; various kinds of phosphoric esters; and alkyl halides such as methyl chloride, methyl bromide and methyl iodide. Among them, p-toluenesulfonic esters such as methyl p-toluenesulfonate, and alkyl halides are particularly preferable.

The reaction of perfluorovinylcarboxylic acid salt (1) and the alkylating agent to be used in the present invention may be carried out in the presence or absence of a solvent. When a solvent is used, various kinds of solvents can be used unless it suppresses the reaction in the present invention. In general, a polar solvent is preferable for good yield. Examples of the solvents to be used for the reaction of the present invention include ketones such as acetone and methyl ethyl ketone; ethers such as tetrahydrofuran, dioxane, ethylene glycol dimethyl ether, diethylene glycol dimethyl ether, triethylene glycol dimethyl ether and tetraethylene glycol dimethyl ether; nitriles such as acetonitrile and propionitrile; amides such as N,N-dimethylformamide, N,N-dimethylacetoamide and N-methylpyrrolidone; dimethyl sulfoxide; sulfolane; and hexamethylphosphorus triamide. Among these solvents, glymes such as ethylene glycol dimethyl ether, diethylene glycol dimethyl ether, triethylene glycol dimethyl ether and tetraethylene glycol dimethyl ether are particularly preferable. No use of solvent may be acceptable if the alkylating agent is liquid at a reaction temperature and a reaction pressure. Amount of the alkylating agent to be used may be an equivalent amount necessary for converting to perfluorovinylcarboxylic acid ester (2), but an excess amount thereof may be used if necessary. In particular, if the alkylating agent is liquid, a large excess amount thereof may be used for the equivalent function of solvent as well.

A reaction temperature and a reaction time depend on kinds of the alkylating agent and the solvent to be used. In general, the reaction temperature is preferably 0–250° C., more preferably 30–150° C., most preferably 50–120° C. The reaction time is, generally, preferably 0.1–50 hours, more preferably 0.2–10 hours, most preferably 0.3–3 hours. Where the alkylating agent is in a liquid state at the reaction temperature after the alkylating agent is charged, the reaction may be carried out in an open system. On the other hand, where the alkylating agent is in a gaseous state at the reaction temperature, the reaction may be carried out in a closed system or under pressure.

After the reaction was terminated, perfluorovinylcarboxylic acid ester (2) can be easily obtained from the reaction mixture by distillation. When an excess amount of alkylating agent is used, the unreacted agent can be recovered and reused.

As a method for producing perfluorovinylcarboxylic acid salt of the general formula (1), although no particular limitation is imposed on it, it is particularly preferred to manufacture perfluorovinylcarboxylic acid salt (1) by thermally decomposing perfluorodicarboxylic acid salt represented by the following general formula (3):

MOCOCF(CF$_3$)O(CF$_2$)$_n$CO$_2$M  (3)

(wherein n represents an integer of 2–3, M represents an alkaline metal, an alkaline-earth metal, a quaternary ammonium group or a quaternary phosphonium group), because perfluorovinylcarboxylic acid salt (1) with a high quality can be obtained according to such a simple manner. The method is included in the scope of the present invention.

It is preferred that perfluorodicarboxylic acid salt of the general formula (3) is sufficiently dried before being subjected to thermal decomposition. Since the content of protic substances such as water in the perfluorodicarboxylic acid salt is reduced by sufficiently drying the perfluorodicarboxylic acid salt, formation of a protonated CF$_3$CHF— group instead of a trifluorovinyl group is prevented, and the yield of perfluorovinylcarboxylic acid salt (1) can be improved. Further, in the thermal decomposition, an aprotic polar solvent which is sufficiently dried is preferably used for the same reason.

In the thermal decomposition reaction of perfluorodicarboxylic acid salt of the general formula (3), the reaction in the presence of aprotic polar solvent can be conducted at a lower temperature of thermal decomposition and in a shorter time, compared to the reaction in the absence of solvent. Therefore, perfluorovinylcarboxylic acid salt (1) can be obtained in good yield under mild conditions. Further, fluorine compounds such as potassium fluoride, which are produced by side reactions in the thermal decomposition reaction, can be easily removed from the reaction mixture by means of such manners as filtration, sedimentation separation and centrifugal separation.

Specific examples of the aprotic polar solvents to be used in the thermal decomposition reaction include ethers such as tetrahydrofuran, dioxane, ethylene glycol dimethyl ether, diethylene glycol dimethyl ether, triethylene glycol dimethyl ether and tetraethylene glycol dimethyl ether; nitriles such as acetonitrile and propionitrile; amides such as N,N-dimethylformamide, N,N-dimethylacetoamide and N-methylpyrrolidone; dimethyl sulfoxide; sulfolane; and hexamethylphosphorus triamide. Among these solvents, glyme type ethers such as ethylene glycol dimethyl ether, diethylene glycol dimethyl ether, triethylene glycol dimethyl ether and tetraethylene glycol dimethyl ether are particularly preferable for a good reaction rate.

In the absence of solvent, the reaction temperature of the thermal decomposition reaction is usually 120–250° C., preferably 140–230° C., more preferably 160–210° C. In the presence of solvent, the reaction temperature of the thermal decomposition reaction, although it depends on the solvent to be used, is usually 60–220° C., preferably 80–200° C., more preferably 100–180° C.

The perfluorodicarboxylic acid salt of the general formula (3) can be obtained by various methods and no limitation is imposed on them. For example, methods known in the art can be used for producing perfluorodicarboxylic acid salt (3) from a compound represented by the following general formula (7):

FCOCF(CF$_3$)O(CF$_2$)$_n$COF  (7)

(wherein n represents an integer of 2–3).

The compound of the general formula (7) is synthesized through an addition reaction of one molecule of hexafluoropropylene oxide (HFPO) to FCO(CF$_2$)$_{n-1}$COF. In this method, a process for isolating the high-purity compound of the general formula (7) from the reaction mixture having a complicated composition is generally required.

As a method for producing the perfluorodicarboxylic acid salt of the general formula (3), it is preferable that perfluorodicarboxylic acid salt (3) is obtained from an acid fluoride represented by the following general formula (4):

FCOCF(CF$_3$)O(CF$_2$)$_n$CO$_2$R'  (4)

(wherein n represents an integer of 2–3; and R' represents an alkyl group having 1–4 carbon atoms)

by a reaction with various alkaline compounds as described below. The inventors found that according to this method, the high-purity perfluorodicarboxylic acid salt (3) can be synthesized by a simple manner, the high-purity perfluorovinylcarboxylic acid salt (1) can be obtained from the perfluorodicarboxylic acid salt and consequently the high-purity perfluorovinylcarboxylic acid ester (2) can be obtained therefrom. As the alkyl group R', an alkyl group having 1–4 carbon atoms is preferably used and methyl group or ethyl group is more preferably used.

The acid fluoride of the general formula (4) to be used in the present invention can be obtained according to methods described in, for example, U.S. Pat. No. 4,138,426. Namely, the acid fluoride can be readily synthesized from HFPO and an acid fluoride represented by the following general formula (8):

FCO(CF$_2$)$_{n-1}$CO$_2$R'  (8)

(wherein n represents an integer of 2–3; and R' represents an alkyl group having 1–4 carbon atoms).

Since the compound of the general formula (8) has only one acid fluoride moiety in the molecule, HFPO can be added at the desired position and the acid fluoride of the general formula (4) can be obtained in high yield.

As methods to obtain the perfluorodicarboxylic acid salt of the general formula (3) from the acid fluoride of the general formula (4), specific examples thereof include a method that an alkaline substance containing M shown in the general formula (3) is added to the acid fluoride for carrying out a saponification reaction so as to directly obtain the perfluorodicarboxylic acid salt, and a method that the acid fluoride is firstly converted into a carboxylic acid diester by reacting it with an alcohol, followed by a saponification reaction with an alkaline substance containing M shown in the general formula (3) so as to obtain the perfluorodicarboxylic acid salt.

In the method that the perfluorodicarboxylic acid salt is directly obtained by adding the alkaline substance containing M shown in the general formula (3) to the acid fluoride, it is preferred that the acid fluoride is mixed with a polar solvent and the alkaline substance is added thereto at desired temperature so as to obtain the perfluorodicarboxylic acid salt. Examples of the alkaline substances containing M shown in the general formula (3) include hydroxides, carbonates, phosphates and the like of alkaline metals or alkaline-earth metals; quaternary ammonium hydroxide; and quaternary phosphonium hydroxide. Among them, hydroxides or the like, wherein M is sodium or potassium, are preferable. In particular, use of perfluorodilcarboxylic acid salt (3) with M being sodium has an advantage in that perfluorovinylcarboxylic acid salt (1) can be obtained at lower temperature of thermal decomposition and/or in a shorter reaction time. The alkaline substance containing M can be usually used in an equivalent amount necessary for the reaction, but an excess amount thereof may be used if necessary. The solvent used in the saponification process is preferably a polar solvent. More specifically, examples of the solvents include ethers such as tetrahydrofuran, dioxane, ethylene glycol dimethyl ether and diethylene glycol dimethyl ether; dimethyl sulfoxide; sulfolane; and water as well. A mixed solvent system containing two or more kinds of solvents may be used if needed. The temperature of the saponification reaction is preferably −20 to 200° C., more preferably 0 to 160° C. Fluorine compounds such as sodium fluoride, which are byproducts formed in the saponification process, can be easily removed from the reaction mixture by filtration, sedimentation separation or centrifugal separation. The perfluorodicarboxylic acid salt can be obtained by distilling the reaction mixture, from which byproducts have been removed.

In the process where the acid fluoride is reacted with the alcohol to be firstly converted into the carboxylic acid diester, the carboxylic acid diester can be easily obtained by mixing and stirring the acid fluoride and the alcohol. As the alcohol, methanol, ethanol, 1-propanol, 2-propanol, butanol and the like are usable. The mixing and stirring temperature is preferably −50 to 150° C., more preferably −20 to 100° C. Thus-obtained carboxylic acid diester can be induced to the perfluorodicarboxylic acid salt according to the substantially same manner as in the case where the perfluorodicarboxylic acid salt is directly obtained by adding the alkaline substance containing M in the general formula (3) to the acid fluoride for the reaction, as described above. Namely, the carboxylic acid diester can be induced to the perfluorodicarboxylic acid salt by carrying put the saponification reaction, according to the substantially same manner, preferably using the substantially same alkaline substance and solvent, as described above.

The perfluorodicarboxylic acid salt can also be obtained by directly adding the acid fluoride to a mixture of the alkaline substance and the alcohol, mixing and stirring it. As the alcohol, methanol, ethanol, 1-propanol, 2-propanol, butanol and the like are usable. The mixing and stirring temperature is preferably −50 to 150° C., more preferably −20 to 120° C. Fluorine compounds such as sodium fluoride, which are byproducts formed in the process, can be easily removed from the reaction mixture by filtration, sedimentation separation or centrifugal separation. The perfluorodicarboxylic acid salt can be obtained by distilling the reaction mixture, from which byproducts have been removed.

As described above, the method to synthesize the high-purity perfluorodicarboxylic acid salt (3) in high yield using the acid fluoride of the general formula (4) as a starting material is novel and included in the scope of the present invention.

According to the method of the present invention, as described above, the perfluorovinylcarboxylic acid ester, which is used as a raw material of an ion-exchange membrane for the chloro alkali process, can be produced in remarkably improved yield compared to conventional methods, and thus the present invention is very useful.

As a method to obtain a perfluorocarboxylic acid polymer from the perfluorovinylcarboxylic acid ester obtained by the present invention and a method to form the diaphragm for the chloro alkali process from the perfluorocarboxylic acid polymer, various known methods can be used.

The present invention will hereinafter be described based on Examples. However, they should not be construed as limiting the scope of the present invention.

In each Example and Comparative Example, yield (%) was obtained by calculating a molar ratio of a product to a starting material.

EXAMPLE 1

(1) Synthesis of Perfluorodicarboxylic Acid Salt 155 g of $FCOCF(CF_3)O(CF_2)_2CO_2CH_3$ was dissolved in 1000 ml of ethylene glycol dimethyl ether and then 233 g of 40% aqueous sodium hydroxide solution was dropwisely added thereto at 0° C. After the addition, the reaction mixture was agitated at room temperature for 5 hours, and subsequently agitated under a reflux condition for additional 5 hours. Formed precipitates were removed by filtration and then the solvent was distilled off under reduced pressure followed by drying at 100° C. to give 170 g of white solid. The solid was identified to be $NaOCOCF(CF_3)O(CF_2)_2CO_2Na$ from the analysis using $^{19}F$-NMR. Yield was 99%.

(2) Synthesis of Perfluorovinylcarboxylic Acid Salt

Under the nitrogen gas stream, 700 ml of anhydrous diethylene glycol dimethyl ether was added to 168 g of $NaOCOCF(CF_3)O(CF_2)_2CO_2Na$ obtained in (1). The mixture was agitated at room temperature and then heated at 150° C. for 1 hour. After the decarboxylation reaction was finished, the formed precipitates were removed using a centrifugal separator. The solvent was distilled off under reduced pressure followed by drying at 120° C. to give 122 g of brown solid. The solid was identified to be $CF_2=CFO(CF_2)_2CO_2Na$ from the analysis using $^{19}F$-NMR. Yield was 96%.

(3) Synthesis of Perfluorovinylcarboxylic Acid Ester 60 g of $CF_2=CFO(CF_2)_2CO_2Na$ obtained in (2) was dissolved in 240 ml of diethylene glycol dimethyl ether. 47 g of methyl p-toluenesulfonate was added to the obtained solution and a reaction was carried out at 90° C. for 3 hours. Subsequently, the solution was subjected to distillation at atmospheric pressure to give 50 g of colorless liquid. The liquid was identified to be $CF_2=CFO(CF_2)_2CO_2CH_3$ from $^{19}F$-NMR and $^1H$-NMR. Yield was 86%.

EXAMPLE 2

24 g of methyl p-toluenesulfonate was added to 20 g of $CF_2=CFO(CF_2)_2CO_2Na$, which was synthesized in the same manner as in Example 1, and reaction was carried out at 90° C. for 2 hours. Subsequently, the obtained solution was subjected to distillation at atmospheric pressure to give 15.5 g of colorless liquid. The liquid was identified to be $CF_2=CFO(CF_2)_2CO_2CH_3$ from the gas chromatography analysis. Yield was 80%.

EXAMPLE 3

31 g of $CF_2=CFO(CF_2)_3CO_2Na$, which was synthesized in the same manner as in Example 1, was dissolved in 150 ml of N,N-dimethylformamide. 14 g of dimethyl sulfate was added to the obtained solution and reaction was carried out at 120° C. for 2 hours. Subsequently, the solution was subjected to distillation at atmospheric pressure to give 25 g of a colorless liquid. The liquid was identified to be $CF_2=CFO(CF_2)_3CO_2CH_3$ from $^{19}F$-NMR and $^1H$-NMR. Yield was 83%.

COMPARATIVE EXAMPLE 1

40 g of $CF_2=CFO(CF_2)_2CO_2Na$, which was synthesized in the same manner as in Example 1, was agitated while adding sulfuric acid (concentration 35%) thereto to obtain a mixture. The addition of the sulfuric acid was continued until the mixture was separated into two layers. Into the isolated lower layer, 200 ml of methanol was added, followed by refluxing for 4 hours. After being cooled, the reaction mixture was washed with water several times, followed by distilling the remaining liquid at atmospheric pressure to give 13 g of a colorless liquid. The liquid was identified to be $CF_2=CFO(CF_2)_2CO_2CH_3$ from the gas chromatography analysis. Yield was 33%.

INDUSTRIAL APPLICABILITY

The present invention is very useful for industrial applications. According to the present invention, perfluorovinylcarboxylic acid ester, which is used for a raw material of the ion-exchange membrane for the chloro alkali process, can be manufactured by a simple procedure in high yield.

What is claimed is:

1. A method for producing a perfluorovinylcarboxylic acid ester, wherein a perfluorovinylcarboxylic acid salt represented by a following general formula (1):

$$CF_2=CFO(CF_2)_nCO_2M \tag{1}$$

(wherein n represents an integer of 2–3; and M represents an alkaline metal, an alkaline-earth metal, a quaternary ammonium group or a quaternary phosphonium group),
is reacted with one or more compounds selected from the group consisting of alkyl esters of strong acids and alkyl halides to obtain a perfluorovinylcarboxylic acid ester represented by a following general formula (2):

$$CH_2=CFO(CF_2)_nCO_2R \tag{2}$$

(wherein n represents an integer of 2–3; and R represents an alkyl group having 1–4 carbon atoms).

2. The method for producing a perfluorovinylcarboxylic acid ester according to claim 1, wherein the perfluorovinylcarboxylic acid salt represented by the general formula (1) is produced by a thermal decomposition of perfluorodicarboxylic acid salt represented by a following general formula (3):

$$MOCOCF(CF_3)O(CF_2)_nCO_2M \tag{3}$$

(wherein n represents an integer of 2–3; and M represents an alkaline metal, an alkaline-earth metal, a quaternary ammonium group or a quaternary phosphonium group).

3. The method for producing a perfluorovinylcarboxylic acid ester according to claim 2, wherein the thermal decomposition of perfluorodicarboxylic acid salt represented by the general formula (3) is carried out in the presence of an aprotic polar solvent.

4. The method for producing a perfluorovinylcarboxylic acid ester according to claim 2 or 3, wherein the perfluorodicarboxylic acid salt represented by the general formula (3) is produced by reacting an acid fluoride represented by the following general formula (4):

$$FCOCF(CF_3)O(CF_2)_nCO_2R' \tag{4}$$

(wherein n represents an integer of 2–3; and R' represents an alkyl group having 1–4 carbon atoms), with an alkaline substance.

5. The method for producing a perfluorovinylcarboxylic acid ester according to claim 2 or 3, wherein the perfluorodicarboxylic acid salt represented by the general formula (3) is produced by reacting an acid fluoride represented by the following general formula (4):

$$FCOCF(CF_3)O(CF_2)_nCO_2R' \tag{4}$$

(wherein n represents an integer of 2–3; and R' represents an alkyl group having 1–4 carbon atoms), with an alcohol to obtain the carboxylic acid diester and saponifying the thus-obtained carboxylic acid diester with an alkaline substance containing M shown in the general formula (3).

6. A method for producing a perfluorovinylcarboxylic acid ester according to claim 1, wherein the alkyl ester of strong acids is one or more compounds selected from the group consisting of p-toluenesulfonic esters, fluoroalkyl sulfonic esters, sulfuric esters, and phosphoric esters.

7. A method for producing a perfluorovinylcarboxylic acid ester according to claim 1 or 6, wherein the perfluorovinylcarboxylic acid salt is reacted with the one or more compounds selected from the group consisting of alkyl esters of strong acids and alkyl halides in aprotic polar solvents.

8. A method for producing a perfluorovinylcarboxylic acid ester according to claim 1 or 6, wherein the perfluorovinylcarboxylic acid salt is reacted with the one or more compounds selected from the group consisting of alkyl esters of strong acids and alkyl halides substantially in the absence of solvents.

* * * * *